United States Patent [19]

Kramer et al.

[11] Patent Number: 5,120,857

[45] Date of Patent: Jun. 9, 1992

[54] UNSATURATED BISIMIDES AND POLYMERS THEREOF

[75] Inventors: Andreas Kramer, Düdingen; Sameer H. Eldin, Fribourg, both of Switzerland

[73] Assignee: Ciba-Geigy Corporation, Ardsley, N.Y.

[21] Appl. No.: 483,282

[22] Filed: Feb. 20, 1990

Related U.S. Application Data

[63] Continuation-in-part of Ser. No. 192,979, May 12, 1988, abandoned.

[30] Foreign Application Priority Data

May 22, 1987 [CH] Switzerland ............... 1992/87

[51] Int. Cl.$^5$ ............................. C07D 209/56
[52] U.S. Cl. ............................. 548/435; 526/262; 526/259
[58] Field of Search ............... 548/435; 526/262, 259

[56] References Cited

U.S. PATENT DOCUMENTS

| | | | |
|---|---|---|---|
| 3,380,964 | 11/1967 | Grundschober et al. | 260/47 |
| 3,562,223 | 2/1971 | Bargain et al. | 260/78 |
| 3,658,764 | 4/1972 | Bargain et al. | 260/78 |
| 4,038,251 | 7/1977 | Forgó et al. | 260/47 |
| 4,515,962 | 5/1985 | Renner | 548/435 |
| 4,604,437 | 8/1986 | Renner | 526/262 |
| 4,666,997 | 5/1987 | Renner et al. | 525/502 |
| 4,678,849 | 7/1987 | Liu et al. | 526/259 |
| 4,709,047 | 11/1987 | Renner et al. | 548/435 |
| 4,726,838 | 2/1988 | Dürr et al. | 71/94 |
| 4,728,742 | 3/1988 | Renner | 548/435 |
| 4,777,236 | 10/1988 | Kramer | 528/322 |
| 4,778,898 | 10/1988 | Vonlanthen et al. | 548/415 |
| 4,782,126 | 11/1988 | Renner et al. | 526/271 |
| 4,847,335 | 7/1989 | Kramer | 525/502 |

OTHER PUBLICATIONS

C.A. 100:156317r (1984).
C.A. 94:84922d (1981).
C.A. 108:55230d (1988).
J. Org. Chem. USSR, 23(5), pp. 869-875 (1987).
C.A. 74:53729d (1971).

*Primary Examiner*—Joseph L. Schofer
*Assistant Examiner*—Alex H. Walker
*Attorney, Agent, or Firm*—JoAnn Villamizar

[57] ABSTRACT

Bisimides of the formula I

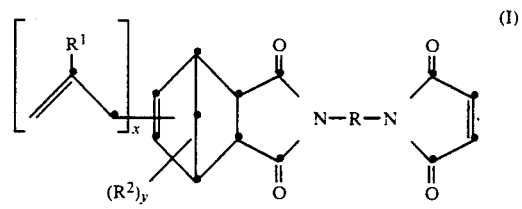

in which, for example, $R^1$ is hydrogen, x is 1, y is zero and R is bis-(1,4-phenylene)-methane are intermediates for the preparation of polymers having excellent physical properties, and are suitable for the production of mouldings, coatings and adhesive joints and, in particular, for the production of prepregs and heat-resistant composite materials.

5 Claims, No Drawings

UNSATURATED BISIMIDES AND POLYMERS THEREOF

This application is a continuation-in-part of application Ser. No. 192,979, filed May 12, 1988, now abandoned.

The invention relates to substituted or unsubstituted bicyclo[2.2.1]-hept-5-ene-2,3-dicarboxylic acid/maleic acid mixed bisimides, to their preparation, to the compositions of matter containing bisimides and to the polymers obtainable therefrom by the application of heat.

U.S. Pat. No. 4,515,962 and U.S. Pat. No. 4,604,437 describe allyl-substituted or methallylsubstituted bicyclo[2.2.1]hept-5-ene-2,3-dicarboximides and their use for the preparation of polymers by heating the imides to temperatures between 180° and 300° C.

It is also known that polymaleimides can, with or without the addition of crosslinking agents, such as diamines or diols, be converted into crosslinked products by heating [cf., for example, U.S. Pat. Nos. 3,562,223, 3,658,764, 3,380,964 and 4,038,251].

U.S. Pat. No. 4,666,997 describes heat-curable compositions of matter consisting of substituted bicyclo[2.2.1]hept-5-ene-2,3-dicarboximides, polymaleimides and, if appropriate, additionally a compound capable of reacting with the polymaleimides.

The present invention relates to bisimides of the formula I

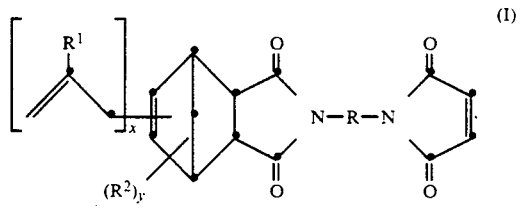

(I)

in which x is zero, 1, 2 or 3, y is zero or an integer from 1 to 6 and $x+y \leq 6$, $R^1$ is hydrogen or methyl and $R^2$ is chlorine, bromine, $C_1$-$C_4$alkyl or benzyl and R is —$C_mH_{2m}$— in which m=2–20, cycloalkylene having 5 to 10 C atoms, bis-(methylene)-cycloalkylene having 7 to 12 C atoms, arylene having 6 to 10 C atoms, bis-(methylene)-arylene having 8 to 12 C atoms or a group of the formula

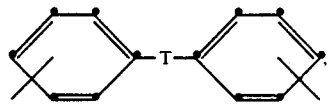

(II)

in which T is methylene, isopropylidene, CO, O, S or $SO_2$.

The bisimides according to the invention are valuable starting materials for polymers which have excellent properties, and are therefore suitable for the production of mouldings, coatings and adhesive bonds and, in particular, for the production of prepregs and heat-resistant composite materials.

Bisimides of the formula I in which $x+y \leq 4$ are preferred, particularly those in which $x+y \leq 2$.

Bisimides of the formula I in which $R^1$ is hydrogen, x is 1 and y is zero are preferred. Bisimides of the formula I in which $R^2$ is $C_1$-$C_3$alkyl or benzyl, y is 1 and x is zero are also preferred.

If the substituent $R^2$ in the bisimides according to the invention is $C_1$-$C_4$alkyl, methyl, ethyl, n-propyl, isopropyl and n-, iso-, sec-and tert-butyl are suitable.

As a group —$C_mH_{2m}$—, R can be linear or branched radicals, such as ethylene, propylene, trimethylene, tetramethylene, hexamethylene and dodecamethylene.

As a group of the formula II, R is preferably attached to the N atoms in the 4,4'-position.

As a cycloalkylene group, R can be cyclopentylene, cyclohexylene, cycloheptylene or cyclooctylene groups, bis-(cycloalkylene)-methane groups or bicyclic systems, for example decalinylene or bicycloheptylene or bicyclooctylene groups. If R is a bis-(methylene)-cycloalkylene radical, suitable cycloalkylene groups are those mentioned above which are substituted by two methylene groups, for example bis-(methylene)-cyclohexane.

As an arylene group having 6 to 10 C atoms, R can be, for example, an m-phenylene, p-phenylene, 1,3-naphthylene, 1,4-naphthylene, 1,5-naphthylene or 2,6-naphthylene group. If R is a bis-(methylene)-arylene radical, suitable arylene groups are those mentioned above which are substituted by two methylene groups.

Preferred bisimides are those of the formula I in which R is —$(CH_2)_p$— in which p=2–12, cyclohexylene, bis-(methylene)-cyclohexane, bis-(cyclohexylene)-methane, phenylene, such as 1,2-, 1,3- and 1,4-phenylene, xylylene, such as 1,2-, 1,3- and 1,4-xylylene, or, in particular, a group of the formula II in which T is methylene, O or $SO_2$.

Bisimides which are particularly preferred are those of the formula I in which R is 1,4-phenylene, 1,4-xylylene or bis-(1,4-phenylene)-methane.

The bisimides according to the invention can be prepared by a Diels-Alder reaction between a bismaleimide of the formula III

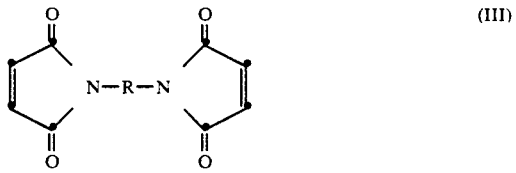

(III)

and a cyclopentadiene of the formula IV

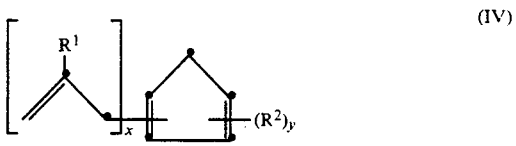

(IV)

the symbols R, $R^1$, $R^2$, x and y being as defined above. The reaction is preferably carried out in an inert solvent suitable for the bismaleimide of the formula (III), for example dioxane, tetrahydrofuran, acetone, methylene chloride, chloroform or toluene, for example by adding the cyclopentadiene of the formula IV dropwise to a solution of the bismaleimide at approx. 20° to 150° C., stirring the reaction mixture for a further 1 to 5 hours and isolating the desired Diels-Alder adduct by removing the solvent. In general, as well as the bisimide according to the invention of the formula I, symmetrical bisimides in which two maleimidyl radicals of the bismaleimide of the formula III have reacted with the cyclopentadiene of the formula IV are also formed in the reaction described, so that, if equimolar amounts of the educts of the formulae III and IV are employed, unreacted bismaleimide of the formula III is also present in the mixture of products. The bisimides of the formula I can be isolated in a pure form, for example by means of HPLC, from the mixtures of products obtained in this way. The said mixtures of products can, however, be employed without further treatment for the preparation of valuable crosslinked polymers.

The educts of the formulae III and IV are known and can be prepared in a known manner. Bismaleimides of the formula III are described, for example, in U.S. Pat. Nos. 3,562,223, 3,658,764, 3,380,964 and 4,038,251, and cyclopentadienes of the formula IV are disclosed, for example, in U.S. Pat. No. 3,560,583.

If desired, the bisimides according to the invention of the formula I can also be prepared in a pure form, for example as follows:

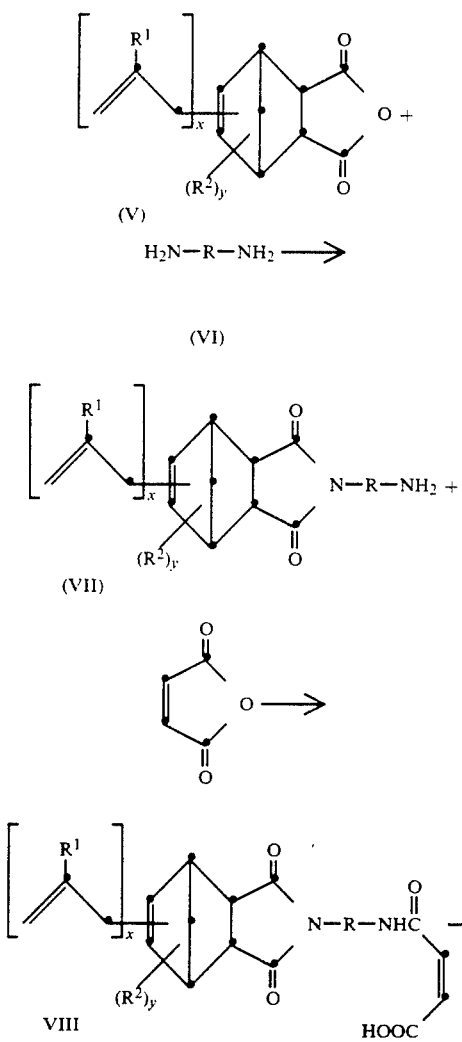

The symbols $R^1$, $R^2$, R, x and y in the compounds of the formulae V to VIII are as defined above.

Anhydrides of the formula V are known and can be prepared, for example, by a Diels-Alder addition of cyclopentadienes of the formula IV onto maleic anhydride. Compounds of this type and their preparation are described in U.S. Pat. No. 3,105,839.

The invention also relates to compositions of matter containing a bisimide of the formula I and obtainable by reacting a bismaleimide of the formula III

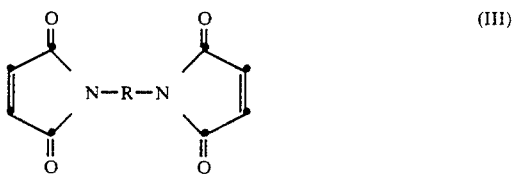

with 0.4 to 1.6 equivalents of a cyclopentadiene of the formula IV

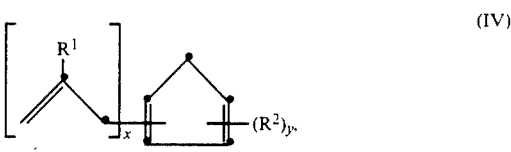

in which the symbols R, $R^1$, $R^2$, x and y are as defined above.

The compositions of matter according to the invention thus contain at least 20 mol % of a bisimide, according to the invention, of the formula I, the remaining components of the compositions of matter being the unreacted bismaleimide of the formula III and the bis-(bicyclo[2.2.1]hept-5-ene-2,3-dicarboximide) formed by the reaction of both the maleimide groups of the imides of the formula III.

Preferred compositions of matter are those in which 0.7 to 1.3, preferably 1, equivalents of the cyclopentadiene of the formula IV are employed per bismaleimide of the formula III.

The compositions of matter according to the invention can, if appropriate, additionally contain 1 to 3, preferably 5 to 25, % by weight, relative to the total mixture, of a compound capable of reacting with the bisimide of the formula I or with the bismaleimide of the formula III. It is possible to employ any known compounds in this regard. Compounds which can react with bismaleimides or with the maleimide group of the bisimides of the formula I are described, for example, in U.S. Pat. No. 4,666,997 as component (c) of the compositions of matter. Diamines and diols, and also phenol and cresol novolaks or mixtures of such compounds are particularly suitable in this regard.

Diamines and diols of the formula IX $$HQ-R'-QH \qquad (IX)$$

in which Q is O or NH and R' is a divalent organic radical having 2-30 C atoms, and also phenol and cresol novolaks or mixtures of such compounds are particularly suitable.

As a divalent organic radical, R' is preferably —$C_pH_{2p}$— in which p=2-20, especially —$(CH_2)p$— in which p=2-12, arylene having 6-10 C atoms, especially m-phenylene, p-phenylene, xylylene, cyclopentylene, cyclohexylene, 1,4-bis-(methylene)-cyclohexylene, the radical of a bicyclohexylmethane or a radical of the formula II. It is particularly preferable for R' to be a radical of the formula II which is attached in the 4,4'-position.

A further class of preferred compounds is formed by alkenyl-substituted phenols and polyols, for example compounds of the formula X

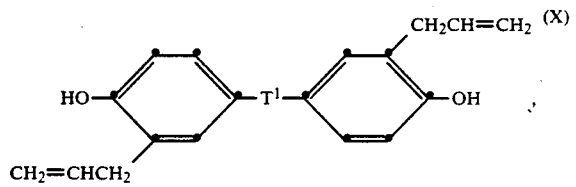

in which $T^1$ is a direct bond, methylene, isopropylidene, O, S, SO or $SO_2$. The following are examples of such compounds: bis-(4-hydroxy-3-allyl)biphenyl, bis-(4-hydroxy-3-allylphenyl)-methane and 2,2-bis-(4-hydroxy-3-allylphenyl)-propane (o,o'-diallylbisphenol A).

As compounds capable of reacting with the bisimides of the formula I or the bismaleimides of the formula III, the compositions of matter according to the invention preferably contain phenol or cresol novolaks, compounds of the formula IXa

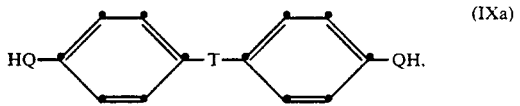

which Q and T are as defined above under the formula IX or II, respectively, and T is, in particular, methylene or isopropylidene, or compounds of the formula X in which $T^1$ is isopropylidene, and also mixtures of the preferred compounds mentioned. The compounds of the formulae IX, IXa and X are known or can be prepared by methods known per se.

Suitable compounds which can react with the bicyclo[2.2.1]hept-5-ene-2,3-dicarboximide group of the bisimides of the formula I are, in particular, the bicyclic imides, containing sulfonyloxy groups and described in EP-A 190,102, of the formula XI

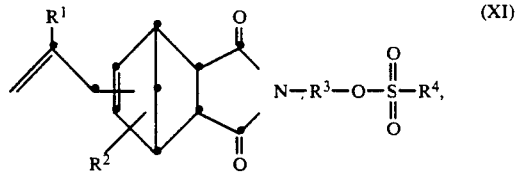

in which $R^1$, $R^2$, $R^3$ and $R^4$ are as defined in EP-A 190,102.

The bisimides according to the invention are starting materials for the preparation of polymers which have excellent physical properties.

The invention also relates to polymers which are obtainable by heating a bisimide of the formula I at a temperature between 100° and 300° C. for 1 to 20 hours.

The curing or processing of the bisimides of the formula I and of compositions of matter containing them can be carried out in an inert organic solvent, but is preferably carried out from the and, if appropriate, in the presence of a curing catalyst. Examples of suitable inert organic solvents are dimethylformamide, dimethylacetamide, N-methylpyrrolidone, toluene, xylenes, methylene chloride, tetrahydrofuran, methyl ethyl ketone and ethylene glycol monoalkyl or dialkyl ethers having 1-4 C atoms in the alkyl groups. Depending on the intended use, examples of suitable curing catalysts are organic peroxides, such as ditert-butyl peroxide, dicumyl peroxide or tert-butyl perbenzoate, or basic catalysts, in particular primary, secondary and tertiary amines, for example diethylamine, tributylamine, triethylamine, benzylamine, N,N,N',N'-tetramethyl-4,4'-diaminodiphenylmethane, N,N-diisobutylaminoacetonitrile or N,N-dibutylaminoacetonitrile, and heterocyclic bases, such as quinoline, N-methylpyrrolidine and imidazole. It is particularly advisable to add basic catalysts of the type mentioned if phenols or polyols are used as the additional component, capable of reacting with the maleimide groups, in the compositions of matter according to the invention. Curing is, in general, carried out at temperatures between 100 ⓡ and 300° C., especially 120° and 250° C.

The bisimides according to the invention and compositions of matter containing them constitute low-melting, solid resins to viscous, liquid resins and are distinguished by high reactivity and good mechanical properties in the products thus cured, such as good flexural strength and impact strength. Products obtained in this manner have high glass transition temperatures and very good resistance to heat and, in addition, are also not very brittle. The bisimides and compositions of matter according to the invention can also be applied readily from the melt, in particular without adding solvents of low volatility, for example for impregnating glass fibre, carbon fibre or aramide fibre fabrics, such as fibre fabrics composed of the poly-(1,4-phenylene terephthalamides) known under the tradename Kevlar Ⓡ.

The bisimides according to the invention and compositions of matter containing them can be used in a versatile manner, for example as laminating resins or electrical resins, as high-temperature adhesives or for the production of coatings or mouldings. They are very particularly suitable for the preparation of prepregs and heat-resistant composite materials.

The invention also relates to the use of the bisimides of the formula I for the production of mouldings, prepregs, laminates, coatings or adhesive joints.

Surprisingly, the mixed (unsymmetrical) bisimides, according to the invention, of the formula I exhibit a higher reactivity when polymerized than either the symmetrical bismaleimides or the symmetrical bis-(bicyclo[2.2.1]hept-5-ene-2,3-dicarboximides) or mixtures of these symmetrical bisimides. In addition, the polymers prepared by crosslinking using the bisimides, according to the invention, of the formula I or the compositions of matter, according to the invention, containing them are distinguished by substantially higher glass transition temperatures.

The invention is illustrated in greater detail by means of the following examples.

EXAMPLE 1

Preparation of the Diels-Alder monoadduct of allylcyclopentadiene and N,N',4,4'-diphenylmethanebismaleimide

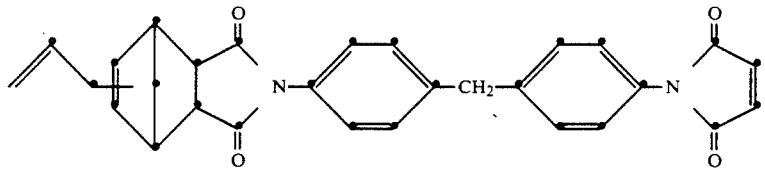

132 g of allylcyclopentadiene (prepared as described in U.S. patent specification No. 3,560,583, Example 1) are added dropwise, at 60°–65° C. and in the course of 30 minutes, to a solution of 358 g of N,N',4,4'-diphenylmethanebismaleimide in 800 ml of dioxane, and the mixture is then stirred for two hours at 60° C. The clear, red-yellow reaction solution is cooled, the solvent is removed by distillation under a water-pump vacuum and the residue is dried for 2 hours under a high vacuum at 80° C. This gives 485 g (99 % of theory) of a yellow-red solid resin having a softening point of 57° C. and a molecular weight, determined by gel permeation chromatography (THF) of 452 ($\overline{M}_n$) or 472 ($\overline{M}_w$). The IR spectrum shows an absorption band at 1710 cm$^{-1}$ (>C=O) and at 1640 cm$^{-1}$ (>C=C<).

| Analysis | % C | % H | % N |
| --- | --- | --- | --- |
| Calculated for $C_{29}H_{24}N_2O_4$ | 74.98 | 5.21 | 6.03 |
| Found | 74.84 | 5.34 | 5.79 |

EXAMPLE 2

Preparation of the Diels-Alder monoadduct of allylcyclopentadiene and N,N',4,4'-diphenyl-ether-bismaleimide

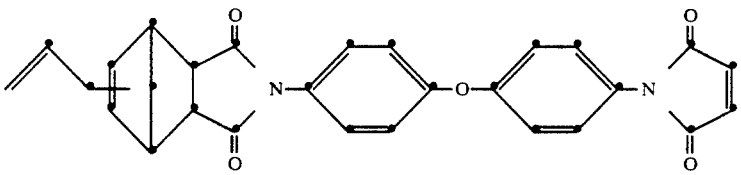

The procedure described in Example 1 is repeated, except that N,N',4,4'-diphenyl-ether-bismaleimide is used instead of the bismaleimide compound employed in Example 1, affording, in quantitative yield, a red-brown solid resin having a softening point of 56° C. and a molecular weight, determined by gel permeation chromatography (THF), of 589 ($\overline{M}_n$) or 6103 ($\overline{M}_w$)

| Analysis | % C | % H | % N |
| --- | --- | --- | --- |
| Calculated for $C_{28}H_{22}N_2O_5$ | 72.09 | 4.75 | 6.00 |
| Found | 71.76 | 5.20 | 5.30 |

EXAMPLE 3

Preparation of the Diels-Alder monoadduct of allylcyclopentadiene and N,N',4,4'-diphenylsulfone-bismaleimide

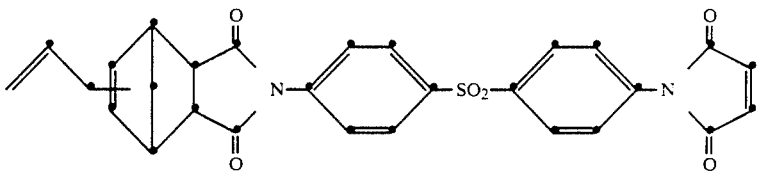

The procedure of Example 1 is repeated, except that the bismaleimide of N,N',4,4'-diaminodiphenyl sulfone is used, affording a red-brown solid resin having a softening point of 49° C. and a molecular weight, determined by gel permeation chromatography (THF), of 763 ($\overline{M}_n$) or 2826 ($\overline{M}_w$).

EXAMPLE 4

Preparation of the Diels-Alder monoadduct of allylcyclopentadiene and N,N',1,6-hexamethylenebismaleimide

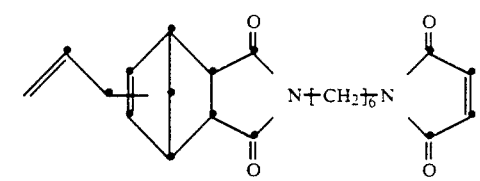

1 mol of allylcyclopentadiene is added dropwise, at 70° C. and in the course of 30 minutes, to a solution of 1 mol of N,N',1,6-hexamethylenebismaleimide in 700 ml of dioxane, and the mixture is then stirred for two hours at 70° C. The clear reaction solution is cooled, and the solvent is removed by distillation on a rotary evaporator. A liquid resin which solidifies on standing is isolated in a quantitative yield. The molecular weight was determined as 440 ($\overline{M}_n$) or 12160 ($\overline{M}_w$) by gel permeation chromatography (THF).

| Analysis | % C | % H | % N |
| --- | --- | --- | --- |
| Calculated for $C_{22}H_{26}N_2O_4$ | 69.09 | 6.85 | 7.32 |
| Found | 69.23 | 6.85 | 6.99 |

EXAMPLE 5

Preparation of the Diels-Alder monoadduct of methylcyclopentadiene and N,N',4,4'-diphenylmethanebismaleimide

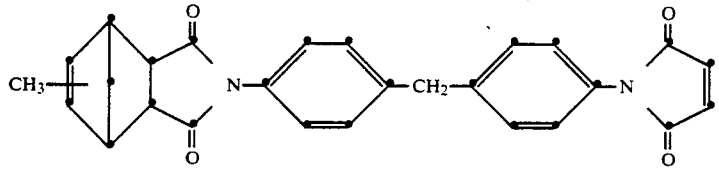

40 g of methylcyclopentadiene (prepared by cracking methylcyclopentadiene dimer) are added dropwise, at 70° C. and in the course of 15 minutes, to a solution of 179 g of N,N',4,4'-diphenylmethanebismaleimide in 500 ml of dioxane, and the mixture is then stirred for two hours at 60° C. The solvent is removed by distillation and the clear, yellow residue is dried for 2 hours under a high vacuum at 120° C. This gives 212 g of a yellow solid resin having a softening point of 65° C. and a molecular weight, determined by gel permeation chromatography (THF), of 422 ($\overline{M}_n$) or 660 ($\overline{M}_w$).

| Analysis | % C | % H | % N |
| --- | --- | --- | --- |
| Calculated for $C_{27}H_{22}N_2O_4$ | 73.96 | 5.06 | 6.39 |
| Found | 73.55 | 5.18 | 6.35 |

EXAMPLE 6

Preparation of the Diels-Alder monoadduct of propylcyclopentadiene and N,N',4,4'-diphenylmethanebismaleimide

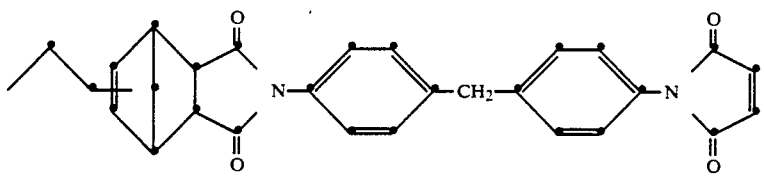

56 g of propylcyclopentadiene (prepared from cyclopentadiene and propylbromide as described in U.S. patent specification No. 3,560,583) are added dropwise, at 70° C. and in the course of 20 minutes, to a solution of 179 g of N,N',4,4'-diphenylmethanebismaleimide in 500 ml of dioxane, and the mixture is then stirred for two hours at 60° C. The solvent is removed by distillation under a waterpump vacuum and the residue is dried for one hour under a high vacuum at 120° C. This gives 227 g (97.5 % of theory) of a reddish solid resin having a softening point of 60° C. and a molecular weight, determined by gel permeation chromatography (THF), of 428 ($\overline{M}_n$) and 433 ($\overline{M}_w$).

| Analysis: | % C | % H | % N |
| --- | --- | --- | --- |
| Calculated for $C_{29}H_{26}N_2O_4$ | 74.66 | 5.62 | 6.00 |
| Found | 73.92 | 5.60 | 5.98 |

EXAMPLE 7

Preparation of the Diels-Alder monoadduct of benzylcyclopentadiene and N,N',4,4'-diphenylmethanebismaleimide

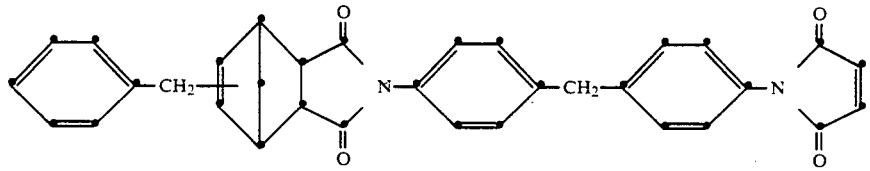

60 g of benzylcyclopentadiene (prepared as described in U.S. patent specification No. 3,560,583, Example 3) are added dropwise, at 60°-65° C. and in the course of 10 minutes, to a solution of 125.3 g of N,N',4,4'-diphenylmethanebismaleimide in 400 ml of dioxane, and the mixture is then stirred for two hours at 60° C. The solvent is then removed by distillation under a waterpump vacuum and the residue is dried for one hour at 120° C. This gives 175 g (97% of theory) of a yellow-red solid resin having a softening point of 67° C. and a molecular weight, determined by gel permeation chromatography (THF), of 466 ($\overline{M}_n$) and 567 ($\overline{M}_w$).

| Analysis | % C | % H | % N |
| --- | --- | --- | --- |
| Calculated for $C_{33}H_{26}N_2O_4$ | 77.03 | 5.09 | 5.44 |
| Found | 76.83 | 5.24 | 5.23 |

USE EXAMPLES I-IV

The bisimides obtained in Examples 1, 5, 6 and 7 are cast, as hot, low-viscosity resins, in steel moulds of dimensions 12×12×0.4 cm, pre-gelling being carried out at 160° C., 200° C. and 220° C. for 3 hours in each case and curing then being carried out at 250° C. for 12 hours. After cooling, test rods are cut out of the clear, red-brown sheets. The results of testing are summarized in the following table.

TABLE

| Use Example | I | II | III | IV |
|---|---|---|---|---|
| Resin: from Example | 1 | 5 | 6 | 7 |
| Flexural strength as specified in ISO 178 (N/mm$^2$) | 110.3 | 49.9 | 48.2 | 17.5 |
| Outer fiber elongation as specified in ISO 178 (%) | 3.7 | 1.4 | 1.5 | 0.5 |
| Impact strength as specified in VSM 77.105 (kJ/m$^2$) | 6.8 | 3.0 | 2.4 | 0.5 |
| Heat distortion point as specified in ISO 75 (°C.) | >250 | >250 | >250 | 230 |
| Glass transition temperature Tg (°C.) (measured by means of TA 2000[1]) | >300 | >300 | >300 | — |
| Water absorption after 1 hour at 100° C. (%) | 0.63 | 0.41 | 0.56 | 0.51 |
| Temperature (°C.) at which 10% loss in weight takes place[2] | 460 | 437 | 450 | 450 |

[1] TA 2000 = differential thermal analysis system TA 2000, by Mettler AG, Greifensee, CH.
[2] Measured by heating a sample in TA 2000; determination of temperature of which 10% of sample are volatilized; rate of heating: 4° C./minute (in air).

USE EXAMPLE V

Preparation of a laminate

The bisimide obtained in Example 1 is used as a 40% solution in methylene chloride to impregnate a C fibre fabric [G814 NT ex CIBA-GEIGY BSD (GB)]. The prepregs are dried for 10 minutes at 100° C. and contain 45.3 % of resin.

Preparation of laminates (10 layers of prepregs measuring 20.5×13.3 cm):

| dwell time in the press: | 3 hours | ⎤ preliminary |
| temperature: | 160° C. | ⎥ curing |
| pressure: | 0.5 kp/mm$^2$ | ⎦ |
| curing temperature: | 220° C. | ⎤ |
| curing time: | 6 hours | ⎥ curing |
| pressure during curing: | 25–30 kp/mm$^2$ | ⎦ |

The laminates have a fibre volume as specified in IS 341/BSD of V$_f$=58.5 %.

The laminate test specimens (55×5×2.5 mm) are found to have a very high glass transition temperature, >350° C., and an excellent resistance to heat:
Interlaminar shear strength as specified in ASTM D 2344 (N/mm$^2$):
30.4 at 23° C.
31.8 at 180° C.
35.6 at 230° C.

The preparation of a pure bisimide of the formula I is described in Examples 8 to 10 below.

EXAMPLE 8

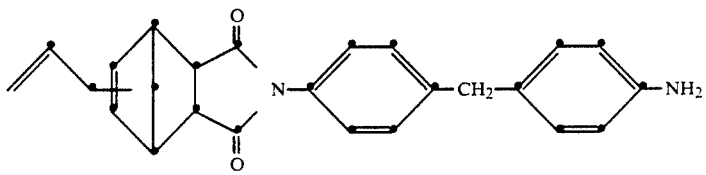

204 g of allylbicyclo [2.2.1]hept-5-ene-2,3-dicarboxylic anhydride (prepared as described in U.S. Pat. No. 3,105,839) and 297 g of 4,4'-diaminodiphenylmethane are initially placed in 750 ml of toluene and heated under reflux for 4 hours under a water separator. The reaction solution is cooled to room temperature and 2 l of 2N hydrochloric acid are added with stirring. A three-phase mixture is formed. The lowest phase, which is not miscible with either toluene or water, is separated off and washed with twice 200 ml of toluene. It is then rendered alkaline with 1N NaOH, and the free base is then extracted with toluene (2×500 ml). The toluene phases are dried over sodium sulfate and filtered, and the solvent is removed by distillation at 80° C. on a rotary evaporator. This gives 255 g of a red solid resin having a melting point of 61°–65° C. and an NH2 content of 2.48 mol/kg (95.5% of theory).

| Analysis: | % C | % H | % N |
|---|---|---|---|
| Calculated for C$_{25}$H$_{24}$N$_2$O$_2$ | 78.10 | 6.29 | 7.29 |
| Found | 77.85 | 6.26 | 7.10 |

EXAMPLE 8

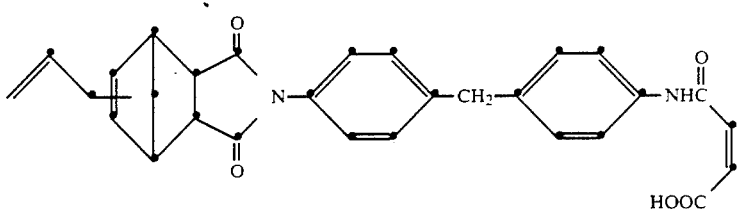

A solution of 40 g of maleic anhydride and 153.6 g of amine (prepared as described in Example 8) in 600 ml of acetone is stirred for 16 hours at room temperature. The precipitate is filtered off, washed with 50 ml of acetone and dried in a vacuum cabinet at 50° C. This gives 134 g (70% of theory) of amic acid in the form of a white powder having a melting point >250° C. and a COOH content of 2.10 mol/kg (100% of theory).

| Analysis: | % C | % H | % N |
|---|---|---|---|
| Calculated for C$_{29}$H$_{26}$N$_2$O$_5$ | 72.19 | 5.43 | 5.81 |

-continued

| Analysis: | % C | % H | % N |
|---|---|---|---|
| Found | 71.86 | 5.40 | 5.80 |

EXAMPLE 10

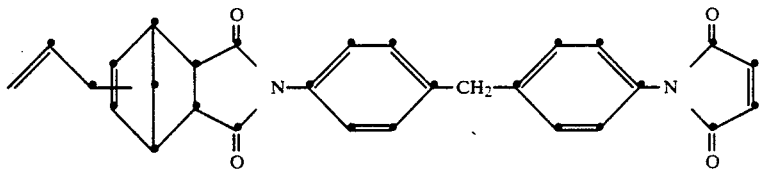

48.2 g of amic acid (prepared as described in Example 9) are added in portions, in the course of 30 minutes and at 70°–75° C., to a solution of 4.8 g of sodium acetate in 50 ml of acetic anhydride. The mixture is then stirred for 60 minutes at 80° C.-85° C. The excess of acetic anhydride is then distilled off and the residue is taken up in 200 ml of methylene chloride. The solution is washed with twice 100 ml of 1N NaOH and twice with water and is dried over sodium sulfate. Removing the methylene chloride by evaporation gives 41.5 g (90 % of theory) of a yellow solid resin having a softening point of 71° C. and a molecular weight, determined by gel permeation chromatography (THF), of 445 ($\overline{M}_n$) or 452 ($\overline{M}_w$).

| Analysis: | % C | % H | % N |
|---|---|---|---|
| Calculated for $C_{29}H_{24}N_2O_4$ | 74.98 | 5.21 | 6.03 |
| Found | 73.74 | 5.28 | 5.93 |

USE EXAMPLE VI

The solid resin prepared as described in Example 10 is poured, in the form of a hot, low-viscosity resin, into a test tube and is cured for 2 hours at 140° C., 2 hours at 180° C., 1 hour at 200° C. and 6 hours at 250° C. This gives a transparent, red-brown solid having a glass transition temperature (determined by means of TMA)[1] of 378° C.

[1] Du Pont 9900 Thermal Analyser

EXAMPLE 11

Diels-Alder adducts formed from allylcyclopentadiene and N,N',4,4'-diphenylmethanebismaleimide a) Example 1 is repeated, except that 0.4 mol of allylcyclopentadiene is used per mol of N,N',4,4'-diphenylmethanebismaleimide instead of the amounts employed in Example 1, affording, in a quantitative yield, a red-brown solid resin having a softening point of 45° C. When subjected to differential thermal analysis (system TA 2000 made by Mettler AG, Greifensee, Switzerland), the resin shows a reaction commencement $T_A$ at 130° C. and a reaction maximum $T_{max}$ at 211° C. The integral heat of reaction ΔH is 240 kJ/kg.

b) Example 1 is repeated, except that 1.6 mol of allylcyclopentadiene is used per mol of N,N',4,4'-diphenylmethanebismaleimide instead of the amounts employed in Example 1, affording, in a quantitative yield, a red-brown solid resin having a softening point of 50° C. When subjected to differential thermal analysis, the resin shows a reaction commencement $T_A$ at 220° C. and a reaction maximum $T_{max}$ at 297° C. The integral heat of reaction is 239 kJ/kg.

USE EXAMPLES VII AND VIII

The solid resins prepared as described in Example 11a and 11b are poured, in the form of a hot, low-viscosity resin, into a test tube and are cured for 3 hours at 160° C., 1 hour at 200° C. and 6 hours at 250° C. This gives transparent, red-brown solids having glass transition temperatures > 300° C.

What is claimed is:

1. A bisimide of the formula I

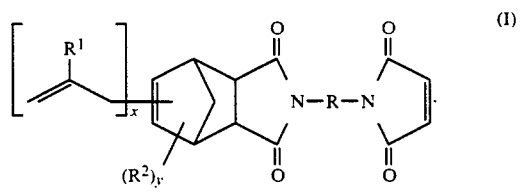

in which x is zero or 1, y is zero or 1 and x+y≦2, $R^1$ is hydrogen or methyl and $R^2$ is $C_1$-$C_3$alkyl or benzyl and R is —$C_mH_{2m}$—in which m=2-20, cycloalkylene having 5 to 10 C atoms, bis-(methylene)-arylene having 8 to 12 C atoms or a group of the formula II

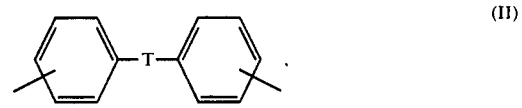

in which T is methylene, isopropylidene, CO, O, S or $SO_2$.

2. A bisimide of the formula I, according to claim 1, in which R is —$(CH_2)_p$—in which p=2-12, cyclohexylene, bis-(methylene)-cyclohexane, bis-(cyclohexylene)-methane, phenylene, xylylene or a group of the formula II according to claim 1 in which T is methylene, O or $SO_2$.

3. A bisimide of the formula I, according to claim 2, in which R is 1,4-phenylene, 1,4-xylylene or bis-(1,4-phenylene)-methane.

4. A composition of matter containing a bisimide of the formula I, according to claim 1, produced by reacting a bismaleimide of the formula II

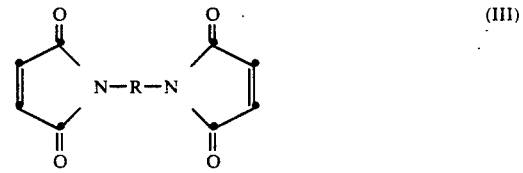

with 0.4 to 1.6 equivalents of a cyclopentadiene of formula IV

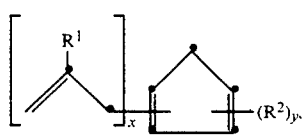 (IV)
in which the symbols R, $R^1$, $R^2$, x and y are as defined in claim 1.
5. A composition of matter as claimed in claim 4, in which 0.7 to 1.3 equivalents of the cyclopentadiene of the formula IV are employed per bismaleimide of the formula III.
* * * * *